United States Patent [19]

Kim

[11] Patent Number: 4,742,088

[45] Date of Patent: May 3, 1988

[54] PHOSPHORUS-CONTAINING NITROGEN COMPOUNDS AS FLAME RETARDANTS AND SYNTHETIC RESINS CONTAINING THEM

[75] Inventor: Youn C. Kim, Kumi, Rep. of Korea

[73] Assignee: Kolon Industries, Inc., Seoul, Rep. of Korea

[21] Appl. No.: 64,219

[22] Filed: Jun. 18, 1987

[30] Foreign Application Priority Data

Sep. 12, 1986 [KR] Rep. of Korea .................. 86-7663

[51] Int. Cl.$^4$ ............................................. C08G 18/14
[52] U.S. Cl. .................................. 521/118; 521/128; 521/129; 524/110; 524/707; 558/82; 558/87
[58] Field of Search ................. 521/118, 128, 129; 524/110, 707; 558/82, 87

[56] References Cited

U.S. PATENT DOCUMENTS 4,113,795  9/1978  Izawa et al. ..................... 558/82

FOREIGN PATENT DOCUMENTS 52-17050    5/1977   Japan .
53-143800  12/1978   Japan .

*Primary Examiner*—Maurice J. Welsh
*Attorney, Agent, or Firm*—M. N. Meller

[57] ABSTRACT

Nitrogen-containing 9,10-dihydro-9-oxa-10-phosphaphenanthrene-10-oxide derivatives are prepared by condensation of the oxide with amines and aldehydes or ketones. They may be used as additive flame retardants or incorporated into synthetic resins such as polyesters and polyurethane foams, by copolymerization to form flame-retardant resins. They may also be used as antioxidants, germicides or herbicides.

19 Claims, No Drawings

PHOSPHORUS-CONTAINING NITROGEN COMPOUNDS AS FLAME RETARDANTS AND SYNTHETIC RESINS CONTAINING THEM

BACKGROUND OF THE INVENTION

1. Field of the Invention

The present invention relates to flame retardants which are nitrogen compounds containing phosphorus and synthetic resins containing them, particularly flame retardants represented by the following general formula (I), which have thermal stability and excellent compatibility with synthetic resins.

It also relates to synthetic resins which have a superior flame retardant property by adding the above flame retardants.

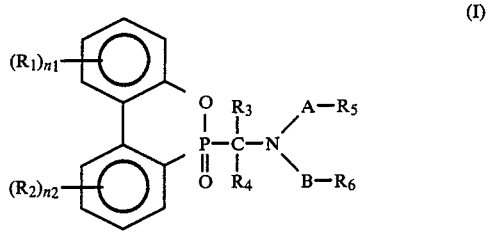

wherein, $R_1$ and $R_2$ may be the same or different and are halogens or hydrocarbon groups containing 1 to 10 carbon atoms, or may be selected from $R_5$ and $R_6$;

$R_3$ and $R_4$ are hydrogen atoms or hydrocarbon groups containing 1 to 10 carbon atoms;

$R_5$ and $R_6$ are hydrogen atoms or functional groups which may be converted to esters;

A and B stand for organic residues of 0 to 10 carbon atoms; and each of $n_1$ and $n_2$ is a number from 0 to 4.

2. Prior Art

Methods for preparing flame retardants and synthetic resins having flame-retardant properties by incorporating them, are known in various forms.

For example, in the case of polyesters, the methods of adding single molecular halogen compounds, or phosphoric esters such as a triphenyl phosphate or phosphoric acids such as a benzenephosphoric acid derivative during the process, are described in JP laid open No. So 56-103217 and No. So 57-125258, and JP publication No. So 52-17050.

Also, the case of polyurethanes etc., JP publications No. So 38-1750, No. So 45-9197, No. So 46-2269, No. So 52-17050 and No. So 56-43056, respectively, disclose processes for preparing flame-retardant synthetic resins by adding a flame retardant such as compounds containing halogen, nitrogen or phosphorus. At that time, the phosphorus content of the synthetic resin had to be more than 10%, preferably 10 to 20% by weight.

But, JP publication No. So 56-47917, U.S. Pat. No. 3,076,010, No. 4,157,436, No. 3,873,496 and No. 3,883,478 disclose methods of adding the above flame retardants in order to prepare flame-retardant synthetic resins, and in these methods the phosphorus content of the synthetic resins, may range from 1 to 20% by weight.

JP publication No. So 40-26335, U.S. Pat. No. 3,288,846, No. 3,257,479, describe methods for preparing flame retardants of nitrogen or phosphorus compounds for flame-retardant synthetic resins.

But, when the flame retardants produced by those prior methods are added to the synthetic resin, not only does the activity of the catalyst required for their process decrease, but also the melting point of the resulting synthetic resin is lowered remarkably. Additionally, crosslinking or gelation occurs due to a reactive functional group. Moreover, the thermal stability and the resistance to acids, bases and water is decreased. Consequently it is impossible to manufacture a product having excellent flame-retardant properties.

Besides the foregoing, methods of adding a flame retardant containing halogen compounds are described in JP laid open No. So 53-143800 and No. So 54-93194. However, in these methods there are many disadvantages in that excess flame retardants must be added and thus poisonous gas is generated. Therefore, the mechanical properties and the processability of the resulting synthetic resins are not good.

JP publication No. So 56-106955 and U.S. Pat. No. 3,660,344 disclose a method of adding nitrogen compounds as flame retardants. However, in those cases the compatibility and the affinity between the flame retardant and the synthetic resin are poor and the flame retardant used may precipitate during the process.

Hence, there are many problems including a lowered thermal stability of the above flame retardant and discoloration of the synthetic resin, etc.

A synthetic resin such as a polyurethane foam has been widely used because of its unique quality. However, it has a disadvantage in that it has a very low level of heat tolerance.

Recently, the importance of the flame-retardant property in polyurethanes has been stressed, especially when the polyurethane is used in cars, trains, or airplanes.

As this occasion demands, when a large quantity of phosphorus or halogen compounds is added by the prior art, the nature of the polyurethane foam becomes poor and very sticky, and it especially decreases in strength. Therefore, its value as a product declines too. And when the flame retardant is used in the additive form, it is readily separated by friction and the flame-retardant effect is reduced.

Also, when the flame retardant is used in reactive form, not only does the thermal stability, the durability and the lasting quality of the polyurethane decrease, but also the similarity to polyurethane is not good and excess flame retardant must be added.

For those reasons, if the flame retardant according to prior methods is used for preparing flame-retardant synthetic resins, the quality of the products is naturally decreased.

Now, the copolymerization of synthetic resins and flame retardants is widely used in order to confer a permanent flame-retardant property to a synthetic resin. Although the foregoing disadvantages in mechanical properties of the products and the processability are slightly reduced, this method cannot completely eliminate the disadvantages. Therefore, any prior methods that have been used do not give satisfactory results, and thus the method must be selected depending upon the circumstances.

A first object of the present invention is to provide flame retardants which are nitrogen compounds containing phosphorus and which are extremely compatible with common synthetic resins, and to enhance to flame-retardant property and thermal stability of a synthetic resin which contains nitrogen and phosphorus in a single molecule.

A second object is to provide the process by which such flame retardants are prepared.

A third object is to provide a synthetic resin which is flame-retardant as a result of the polymerization of the flame retardants with a polymer when the synthetic resin is prepared.

SUMMARY OF THE INVENTION

The flame retardant according to the present invention, represented by the following formula (I), comprises 9,10-dihydro-9-oxa-10-phosphaphenanthrene-10-oxide which may have substituents in a benzene ring (hereinafter, referred to as the first component) and a nitrogen compound (the second component) represented by the following formula (II), and a compound having a carbonyl functional group (a third component) represented by the following formula (III).

It is prepared by the condensation of these components within a temperature range of 50° to 200° C. in a suitablesolvent.

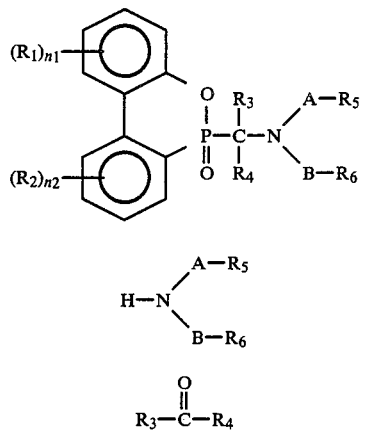

wherein, $R_1$ and $R_2$ may be the same or different and are a halogen or a hydrocarbon group with 1–10 carbon atoms and may be selected from $R_5$ and $R_6$;

$R_3$ and $R_4$ are hydrocarbon groups with 1–10 carbon atoms or hydrogen atoms;

$R_5$ and $R_6$ are hydrogen atoms or functional groups which may be converted to esters;

A and B stand for organic residues of 0 to 10 carbon atoms;

Each of $n_1$ and $n_2$ in a number from 0 to 4.

The present invention also includes synthetic resins containing the flame retardant represented by foregoing formula (I), provided that the synthetic resins contain 500 to 50,000 ppm of phosphorus atoms and 500 to 25,000 ppm of nitrogen atoms.

Flame-retardant synthetic resins according to this invention comprise, for example, flame-retardant polyesters or polyurethane foams. For flame-retardant polyurethane foams $R_5$ and $R_6$ of formula (I) are hydrogen groups.

DETAILED DESCRIPTION OF THE INVENTION

In the present invention, the second component represented by formula (II), is a nitrogen compound having reactive hydrogen groups, such as ammonium, primary amine or secondary amine.

For example, the primary amine may be methylamine, ethylamine, propylamine, butylamine, decylamine, aniline, furfurylamine, naphthylamine, glycine, glutamic acid, monomethanolamine, monoethanolamine or phenylenediamine; the secondary amine may be dimethylamine, diethylamine, methylethylamine, dipropylamine, dimethanolamine, diethanolamine, phenylbenzylamine or their water soluble salts.

The third component represented by formula (III), which has carbonyl functional groups, may include either aldehyde or ketone compounds.

If either of $R_3$ or $R_4$ in formula (III) is a hydrogen atom, the formula then represents aldehyde compounds such as formaldehyde, acetaldehyde, benzaldehyde, chloroaldehyde, aminobenzaldehyde or naphthaldehyde. On the other hand if both of $R_3$ and $R_4$ in formula (III) are organic radicals, the formula represents ketone compounds such as methyl ethyl ketone, acetone, acetophenone, benzophenone, 2-pentanone, 3-pentanone.

A solvent which dissolves the first component and the second component may be selected from among polar solvents such as dimethyl sulfoxide (DMSO), N,N-dimethylformamide (DMF), butanol, ethylene glycol, dioxane, and water.

In this process, the reaction temperature must range from 50° to 200° C. in accordance with the selected solvent, for example, when water is used as the solvent, the reaction temperature must range between 90° and 100° C.

New nitrogen compounds containing phosphorus, the flame retardant of the present invention, can be prepared according to the method where the first component and the second component are dissolved together in a suitable solvent, after which the third component is added thereto at a temperature of 50° to 200° C.

A specific example of this process is as follows: Both 9,10-dihydro-9-oxa-10-phosphaphenanthrene-10-oxide (the first component) and diethanol (the second component) in equimolar quantities are dissolved in a suitable quantity of water. Thereafter, the same number of moles of formaldehyde (the third component) are slowly added to the resulting aqueous solution whose temperature is maintained between 90° and 100° C. At this time, a solvent selected from among dioxane, ethylene glycol, butanol, DMF and DMSO may be also used instead of water. The above mentioned formaldehyde generally designates a formalin solution, but a paraformaldehyde or gaseous state of formaldehyde may also be used, preferably in an amount of 0.1 to 1.1 equivalents.

Specific examples of the new nitrogen compounds containing phosphorus represented by the above formula (I) are as follows;

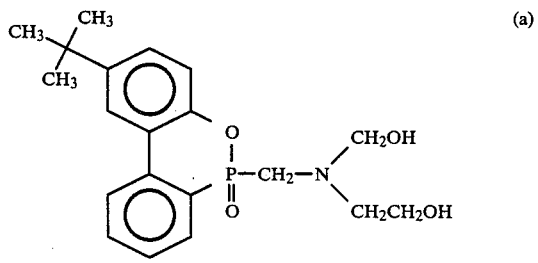

(b)
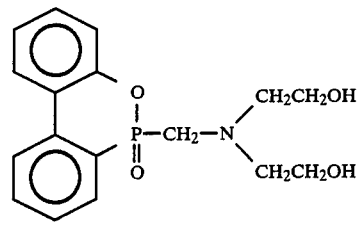

(c)
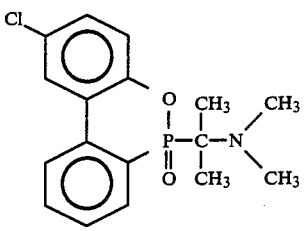

(d)
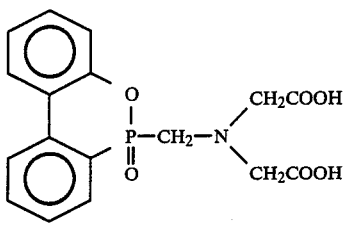

(e)
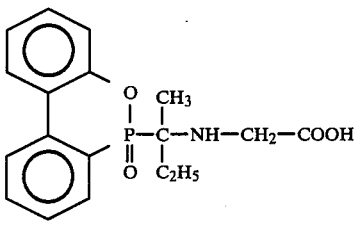

(f)
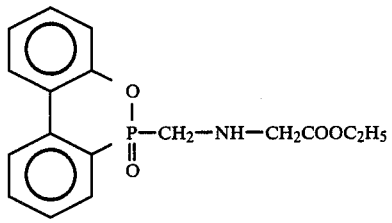

(g)
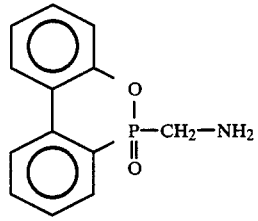

A flame-retardant synthetic resin, for example, a polyester can be prepared from a dicarboxylic acid, a diol and the nitrogen compound containing phosphorus represented by the above general formula (I).

The reaction conditions needed to prepare the polyester, namely ester interchange, esterification and polycondensation can be carried out according to known methods. When using terephthalic acid as the dicarboxylic acid and ethylene glycol as the diol for preparing the polyester, the ester interchange reaction is carried out at a temperature of 140° to 240° C. with a catalyst such as an alkali metal or alkaline earth metal, or metal compound of zinc, manganese, titanium, cobalt etc. After that, the esterification proceeds under the following conditions; temperature of 200° to 230° C., pressure of 5 kg/cm², and a metal compound as a catalyst as used in the foregoing ester interchange reaction. In the final step of preparation of the polyester, the resulting products are polycondensed in the presence of metal compounds such as antimony or germanium or titanium at a temperature from 250° to 320° C. and a vacuum less than 1 mmHg.

The flame-retardant product may contain additives, for example, an ester-bond inhibitor such as a common organic amine or organic amidocarbonate; a pigment such as carbon black or titanium oxide; a stabilizer, plasticizer, or an electric charge inhibitor, etc.

According to the present invention as described above, even if the phosphorus content of the flame-retardant polyester is half that of the prior art, an excellent flame-retardant polyester can be prepared due to the synergism of the nitrogen and phosphorus atoms. In addition, the flame retardant represented by the above formula (I), is capable of exhibiting not only the flame-retardant synergism of the nitrogen and phosphorus atoms, but also thermal stability because the phosphorus atoms form a ring. Moreover, it is extremely compatible with polyesters because its chemical structure is similar to the basic structure of a polyester.

When preparing a flame-retardant polyurethane foam which is a synthetic resin of the present invention, if the polyether polyol or polyester polyol is quickly mixed with an equal amount of polyisocyanate, a flame retardant, a foaming agent, a catalyst and an oil emulsifying agent, then the resulting mixture will foam. Then it is hardened to finish the process of preparing the polyurethane foam. In this case, all or part of the polyisocyanate and polyether polyol or polyester polyol may be reacted with each other before these are mixed with the other components.

The polyether polyol used in the present invention is prepared by addition polymerization of an alkylene oxide and an initial compound containing more than two active hydrogen atoms.

The initial compound may be, for example, ethylene glycol, propylene glycol, glycerine, pentaerythritol, ethylenediamine or sorbitol etc., and examples of the above alkylene oxide may be ethylene oxide, propylene oxide, styrene oxide, butylene oxide, or epichlorohydrin, etc.

The polyeser polyol used in the present invention is prepared by polycondensation of a glycol and a polybasic acid and the initial compound containing more than two reactive hydrogen atoms. The initial compounds are the same as for the polyether polyols. But, the glycol may be selected from among ethylene glycol, propylene glycol, butanediol, hexanediol, or polyglycolethers, and the polybasic acid may be selected from among adipic acid, fumaric acid, succinic acid, thiodiglycolic acid etc.

The polyisocyanate used in the invention is represented by the formula R (NCO)n, in which the average of n is between 1.5 and 3, where R stands for alkyl, aryl, or a substituted alkyl or aryl group. Examples of the compounds represented by the above formula include tolylenediisocyanate (TDI), diphenylmethyldiisocyanate (MDI), polyethylenepolyphenylenediisocyanate and their mixtures.

In the present invention, the catalysts may be metal compounds such as stannous octoate, stannous oleate, octyl plumbic acid; but it is preferable to use amine compounds such as triethylamine, diethylenetriamine, tetramethylethyleneamine, dimethylethanolamine.

As the foaming agent, water or a volatile solvent-foaming for example, monofluorotrichloromethane or methylenechloride, can be used.

The silicone oil emulsifying agent should be chosen in accordance with the proposed use of the resulting polyurethane foam.

The synthetic resin of the present invention, which contains the nitrogen compound containing phosphorus represented by the above formula (I), is prepared according to the known methods of preparing polyesters or polyurethane foam. However the phosphorus content of the resulting product must be from 500 to 50,000 ppm, and the nitrogen content from 500 to 25,000 ppm.

This new nitrogen compound containing phosphorus according to the present invention may be used not only as an additive or reactive flame retardant, but also as an antioxidant or a germicide or a herbicide, and has the following characteristics:

First, it permits synergism of the flame-retardant effect because phosphorus and nitrogen are contained in a single molecule.

Second, it has not only excellent compatibility with synthetic resins, but also thermal stability because the phosphorus atom which is not heat stable is joined with a phenanthrene chain which is stable.

Third, it is predominantly resistant to water, acids and bases because the phosphorus atom is firmly bonded to a carbon atom of a benzene ring.

Fourth, if it is substituted with halogen atoms or a large alkyl group which can cause steric hindrance, an excellent flame-retardant polyester or polyurethane foam can be prepared by using only a small quantity of it, because nitrogen, phosphorus and halogen atoms exhibit both flame-retardant synergism and antioxidizing properties.

This invention is illustrated by the following Examples, but should not be construed to be limited thereto.

EXAMPLE 1

216 g of 9,10-dihydro-9-oxa-10-phosphaphenanthrene-10-oxide and 54 g of ammonium chloride are dissolved in 100 cc of water in a 4-neck flask (1 l), and 90 g of 37% formalin is added to the solution keeping the temperature at 90° to 100° C. for 20 minutes. The mixture is agitated at the above temperature for 1 hour, then cooled to room temperature and left for 24 hours.

The resulting precipitate, which is white, is filtered by a vacuum filter using 22 cc of distilled water in order to remove the remaining moisture.

And then the desired material represented by the above formula (g) is obtained, which has a melting point of 70° to 75° C. and is analyzed as follows;

(1) Results of elemental analysis

---
C: 63.5% (theoretical value: 63.6%)
H: 4.9% (theoretical value: 4.9%)
P: 12.5% (theoretical value: 12.5%)
N: 5.6% (theoretical value: 5.7%)
---

(2) Results of infrared spectroscopic analysis $\nu NH_2$: 3,300 cm$^{-1}$ S,
$\nu$P-C: 1,420 cm$^{-1}$ S,
$\nu$P=O: 1,110 cm$^{-1}$ S, (3) Results of nuclear magnetic resonance analysis (CD$_3$OD, ppm)

7.1–8.2 (8H, m, arom)
4.2 (2H, d, —P—CH$_2$—, J=5 Hz)
2.8 (2H, S, —NH$_2$)

EXAMPLE 2

216 g of 9,10-dihydro-9-oxa-10-phosphaphenanthrene-10-oxide and 105 g of ethanolamine are dissolved in 150 cc of water using the same apparatus as in Example 1, and 33 g of paraformaldehyde is added to the solution at a temperature of 90° to 100° C. for 30 minutes. Then, the mixture is agitated for 1 hour while maintaining a temperature of 90° to 100° C., and dried under vacuum of 10 to 230 torr. After cooling to room temperature, the desired material represented by the above formula (b), which is very viscous, colorless, and transparent, is obtained. It is analyzed as follows;

(1) Results of elemental analysis

---
C: 61.0% (theoretical value: 61.2%)
H: 6.1% (theoretical value: 6.0%)
P: 4.1% (theoretical value: 4.2%)
N: 9.2% (theoretical value: 9.3%)
---

(2) Results of infrared spectroscopic analysis
$\nu$—OH: 3,500 cm$^{-1}$ S,
$\nu$P-C: 1,440 cm$^{-1}$ S,
$\nu$P=O: 1,120 cm$^{-1}$ S, (3) Results of nuclear magnetic resonance analysis CD$_3$OD; ppm)

7.2–8.2 (8H, m, arom)
4.0 (4H, t, —O—CH$_2$, J=4 Hz)
3.8 (2H, d, P—CH$_2$—, J=5 Hz)
3.3 (4H, t, —N—CH$_2$—, J=4 Hz)

EXAMPLE 3

272 g of 6-t-amyl-9,10-dihydro-9-oxa-10-phosphaphenanthrene-10-oxide and 91 g of hydroxymethyl-hydroxyethylamine and 100 cc (35% solution) of hydrochloric acid are dissolved in 200 cc of water using the same apparatus as in Example 1 and 33 g of paraformaldehyde is added to the solution at a temperature of 90° to 100° C. for 30 minutes.

Then, the mixture is agitated for 1 hour while maintaining a temperature of 90° to 100° C., and dried under a vacuum of 10 torr.

After cooling to room temperature, the desired material represented by the above formula (a), which is very viscous, colorless and transparent, is obtained.

It is analyzed as follows:
(1) Results of elemental analysis

---
C: 63.7% (theoretical value: 63.8%)
H: 7.0% (theoretical value: 6.9%)
N: 3.7% (theoretical value: 3.7%)
P: 8.1% (theoretical value: 8.2%)
---

(2) Results of infrared spectroscopic analysis
$\nu$OH: 3,500 cm$^{-1}$ S,
$\nu$P-C: 1,450 cm$^{-1}$ S,
$\nu$P=O: 1,180 cm$^{-1}$ S, (3) Results of nuclear magnetic resonance analysis CD$_3$OD; ppm)

7.2–8.2 (7H, m, arom)
4.3 (2H, s, —N—CH$_2$—O—)
4.0 (2H, t, —O—CH$_2$, J=4 Hz)
3.8 (2H, d, —P—CH$_2$—, J=5 Hz)
3.3 (2H, t, —N—CH$_2$—, J=4 Hz)
1.0 (9H, s, —CH$_3$)

EXAMPLE 4

251 g of 6-chloro-9,10-dihydro-9-oxa-10-phosphaphenanthrene-10-oxide and 82 g of dimethylamine hydrochloride are dissolved in 200 cc of water using the same apparatus as in Example 1 and 116 g of acetone is added to the solution at a temperature of 90° to 100° C. for 30 minutes.

Then, the mixture is agitated for 1 hour while maintaining a temperature of 90° to 100° C., and dried under a vacuum of 10 torr.

After cooling to room temperature the desired material represented as the above formula (c), which is very viscous, is obtained.

(1) Results of elemental analysis

| |
|---|
| C: 60.4% (theoretical value: 60.6%) |
| H: 5.7% (theoretical value: 5.6%) |
| N: 4.1% (theoretical value: 4.2%) |
| P: 9.4% (theoretical value: 9.2%) |

(2) Results of infrared spectroscopic analysis
$\nu$OH 3,500 cm$^{-1}$ S,
$\nu$P-C; 1,420 cm$^{-1}$ S,
$\nu$P=O 1,140 cm$^{-1}$ S,
$\nu$P-C; 1,420 cm$^{-1}$ S, (3) Results of nuclear magnetic resonance analysis CD$_3$OD; ppm)
7.2–8.2 (7H, m, arom)
2.5 (6H, s, —N—CH$_3$—)
1.0 (6H, s, —C—CH$_3$—)

EXAMPLE 5

1 kg of dimethyl terephthalate and 720 g of ethylene glycol, 60 g of the flame retardant prepared by the above Example 2, 0.5 g zinc acetate and 0.6 g antimony trioxide are placed together in an autoclave, and heated to a temperature of 140° C. for 2 hours for the ester interchange. After that, the temperature of the system is increased to 280° C., and the pressure is reduced to 0.2 mmHg, over a period of 45 minutes. The mixture is continuously reacted under those conditions for 1 hour.

The resultant polymer contains 0.3% phosphorus and 0.15% nitrogen, and has an inherent viscosity of 0.59, and a melting point of 258° C.

The fiber, manufactured by spinning the above polymer with an extrusion type-spinner according to a known method at 290° C., is stretched to 3.8 times its length on a heating plate whose temperature is 87° C. The product shows an intensity of 5.1 g/d and a expansibility of 38%.

In order to test the flame-retardant properties of the product, a sample is ignited, but it is not burned entirely until after being ignited seven times repeatedly.

In this invention, the flame-retardant property of the product is shown by the average of five experimental values which are the ignition times attempted to entirely burn the samples. The samples are knitted fiber spun according to the common method, and 1 g of each is cut into 10 cm lengths. They are inserted in a coil of 10 mm thickness at a 45 degree angle, and then entirely burned from the bottom where they were ignited.

COMPARATIVE EXAMPLE 1

A polymer is prepared by the same method as Example 3, but excludes the flame retardant represented by the above formula (b). Samples of the resultant product are entirely burned when they are ignited just one time respectively.

COMPARATIVE EXAMPLE 2

A polymer is prepared by the same method as Example 3, but 50 g of the compound represented by the following formula (A) is added instead of the flame retardant used in Example 3.

The resulting product contains 0.3% of phosphorus, and each of the samples is entirely burned after being ignited three times.

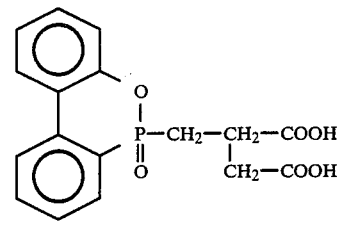

(A)

EXAMPLE 6

1 kg of a polyether polyol is placed in a 2 l polyethylene beaker, and then the first 8 components listed below are added therein. The resulting mixture is agitated and the temperature is adjusted to 25° C. Then TDI-80, at a temperature of 25° C., is added and the mixture is agitated at 4,000 rpm for 5 seconds, and charged into a stainless steel cup.

Consequently, foaming of the mixture begins within 20 seconds and is finished in approximately 100 seconds. Then the mixture is transfered to a kiln, and allowed to harden at a temperature of 120° C. for 15 minutes.

The product is left at room temperature for more than 24 hours, after which its physical properties are measured.

| (Components) | |
|---|---|
| polyether polyol | 100 parts by weight |
| water | 4.8 parts by weight |
| monofluorotrichloromethane | 8 parts by weight |
| Silicon oil L-520 | 1.3 parts by weight |
| triethylenediamine | 0.1 parts by weight |
| stannous octoate | 0.2 parts by weight |
| N—ethylmorpholine | 0.2 parts by weight |
| flame retardant (the compound of the above formula (I)) | Variable |
| TDI - 80 | 105 parts by weight |

(Flame Test)

A flame test consists of the measurement of burned length (mm) according to ASTM (American Society for Testing and Materials) D 1692-68 and MVSS 302 (Motor Vehicle Safety Standard No. 302). In the case of the ASTM D 1692-68 Test, the length from the first sign of ignition to the second sign on the tested pieces is fixed at 100 mm and in the case of the MVSS 302 Test, fixed at 254 mm.

In order to compare the flame-retardant property of each tested piece, the products manufactured by the prior art and the present invention are tested together as shown in Table 1, wherein parts stands for values per 100 parts of polyether polyol.

TABLE 1

| Part | according to the invention | | | | | | | according to the prior art | | | |
|---|---|---|---|---|---|---|---|---|---|---|---|
| type of polyether polyol | A | A | B | A | B | A | B | A | A | B | B |
| flame retardant | | | | | | | | | | | |
| representative formula | (I)-a | (I)-a | (I)-a | (I)-b | (I)-b | (I)-c | (I)-c | P-1 | P-2 | P-1 | P-1 |
| quantity (parts) | 1 | 2 | 1 | 1 | 1 | 1 | 10 | 1 | 1 | 2 | 2 |
| foam density (g/cm³) | 20.1 | 20.3 | 19.6 | 19.7 | 19.9 | 20.4 | 20.2 | 20.1 | 19.8 | 20.3 | 20.2 |
| burned length (mm) | | | | | | | | | | | |
| ASTM D 1692 68 | 22 | 11 | 20 | 16 | 17 | 18 | 19 | 211 | 150 | 110 | 70 |
| MVSS 302 | 10 | 2 | 9 | 4 | 8 | 7 | 8 | 340 | 195 | 260 | 103 |

(notes)
A: glycerine
B: pentaerythritol
I-a: Compound of formula (I) in which $n_1$, $n_2$ are zero
I-b: Compound of formula (I) in which $n_1$, $n_2$ are 1, and $R_1$, $R_2$ are Cl
I-c: Compound of formula (I) in which $n_1$, $n_2$ are 1, and $R_1$, $R_2$ are 3-amyl.
P-1: Tris-chloroethyl phosphate
P-2: Fyrol 6 (the product of Stauffer Chemical Co.)

The foregoing Examples and Comparative Example show the following: a flame-retardant polyester, a flame-retardant resin prepared according to this invention, not only has at least equal physical and mechanical properties in comparison with ones which don't contain a flame retardant, but also possesses an excellent flame-retardant property, and is especially easily dyed.

The flame-retardant polyester may be used as a fiber as well as a board or film, a molded plastic and as other products.

In the above table (I), the flame-retardant polyurethane foam according to this invention, also, shows a much shorter burned length than prior ones, namely it has a superior flame-retardant property.

I claim:

1. A flame retardant represented by the following formula (I),

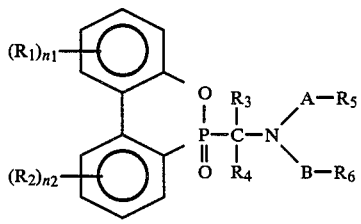

(I)

wherein
$R_1$ and $R_2$ may be the same or different and are halogen atoms or hydrocarbon groups with 1 to 10 carbon atoms or may be selected from $R_5$ and $R_6$;
$R_3$ and $R_4$ are hydrogen atoms or hydrocarbon groups with 1 to 10 carbon atoms;
$R_5$ and $R_6$ are hydrogen atoms or functional groups which may be converted to esters;
A and B stand for organic residues of 0 to 10 carbon atoms;
each of $n_1$ and $n_2$ is a number from 0 to 4.

2. A method for preparing the flame retardant represented by the following formula (I), which comprises condensing a 9,10-dihydro-9-oxa-10-phosphaphenanthrene-10-oxide compound with a nitrogen compound containing reactive hydrogens represented by the following formula (II), and with a compound containing a carbonyl functional group represented by the following formula (III) at a temperature of 50° C. to 200° C. in a suitable solvent,

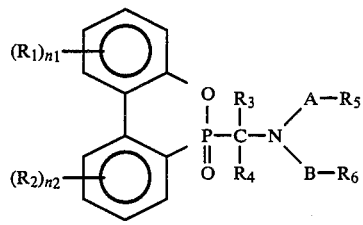

(I)

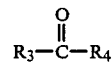

(II)

(III)

$$R_3-\overset{O}{\underset{\|}{C}}-R_4$$

wherein,
$R_1$ and $R_2$ may be the same or different and are halogen atoms or hydrocarbon groups with 1 to 10 carbon atoms, or may be selected from $R_5$ and $R_6$;
$R_3$ and $R_4$ are hydrogen atoms or hydrocarbon groups with 1 to 10 carbon atoms;
$R_5$ and $R_6$ are hydrogen atoms or functional groups which may be converted to esters;
A and B stand for organic residues of 0 to 10 carbon atoms;
each of $n_1$ and $n_2$ is a number from 0 to 4.

3. The method according to claim 2, in which the solvent is selected from the group consisting of water, dioxane, ethylene glycol, dimethylformamide and dimethylsulfoxide.

4. The method according to claim 2, in which the nitrogen compound containing reactive hydrogens is selected from the group consisting of primary amines and secondary amines.

5. The method according to claim 2, in which the compound containing a carbonyl functional group is selected from the group consisting of aldehydes and ketones.

6. A flame retardant synthetic resin which comprises a synthetic resin composition and a flame retardant of following formula (I), provided that the phosphorus content of the resulting synthetic resin is from 500 to 50,000 ppm and the nitrogen content is 500 to 25,000 ppm,

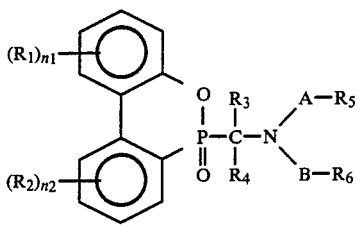

wherein,

R$_1$ and R$_2$ may be the same or different and are halogen atoms or hydrocarbon groups with 1 to 10 carbon atoms, or may be selected from R$_5$ and R$_6$;

R$_3$ and R$_4$ are hydrogen atoms or hydrocarbon groups with 1 to 10 carbon atoms;

R$_5$ and R$_6$ are hydrogen atoms or functional groups which may be converted to esters;

A and B stand for organic residues of 0 to 10 carbon atoms;

each of n$_1$ and n$_2$ is a number from 0 to 4.

7. The resin according to claim 6, which is a polyester.

8. The resin according to claim 6, which is a polyurethane foam.

9. The resin according to claim 8, prepared by mixing a polyether polyol or polyester polyol, a polyisocyanate, a flame retardant, a foaming agent, a catalyst and an oil emulsifying agent to form a uniform mixture, and hardening the mixture.

10. The resin according to claim 8, prepared by first mixing all or part of a polyisocyanate and polyester polyol, subsequently adding a flame retardant, a foaming agent, a catalyst and an oil emulsifying agent to form a uniform mixture and hardening the mixture.

11. The resin according to claim 9, wherein the polyether polyol is prepared by addition polymerization of an alkylene oxide and an organic compound containing more than two reactive hydrogen atoms.

12. The resin according to claim 9, wherein the polyester polyol is prepared by polycondensation of a glycol and a polybasic acid and an organic compound containing more than two reactive hydrogen atoms.

13. The resin according to claim 10, wherein the polyester polyol is prepared by polycondensation of a glycol and a polybasic acid and an organic compound containing more than two reactive hydrogen atoms.

14. The resin according to claim 9, in which the polyisocyanate is represented by the formula R(NCO)n, wherein R is an alkyl or aryl, or a substituted alkyl or aryl and the average of n is between 1.5 and 3.

15. The resin according to claim 10, in which the polyisocyanate is represented by the formula R(NCO)n, wherein R is an alkyl or aryl, or a substituted alkyl or aryl and the average of n is between 1.5 and 3.

16. The resin according to claim 6, in which the resulting synthetic resin is polyurethane which is prepared by adding a flame retardant of the above formula (I) wherein R$_5$ and R$_6$ are —OH radicals.

17. A board formed from the synthetic resin according to claim 6.

18. A film formed from the synthetic resin according to claim 6.

19. A molded plastic formed from the synthetic resin according to claim 6.

* * * * *